(12) United States Patent
Chi

(10) Patent No.: US 8,380,298 B2
(45) Date of Patent: Feb. 19, 2013

(54) MAGNETIC ACUPUNCTURE NEEDLE

(76) Inventor: Tom Chi, South Fallsburg, NY (US)

( * ) Notice: Subject to any disclaimer, the term of this patent is extended or adjusted under 35 U.S.C. 154(b) by 888 days.

(21) Appl. No.: 11/947,716

(22) Filed: Nov. 29, 2007

(65) Prior Publication Data

US 2009/0143811 A1    Jun. 4, 2009

(51) Int. Cl.
*A61H 39/02* (2006.01)
*A61B 5/05* (2006.01)
*A61B 17/34* (2006.01)

(52) U.S. Cl. .......... 600/548; 600/547; 606/189

(58) Field of Classification Search ........... 600/300, 600/372, 373, 546, 547, 548, 550, 554, 555, 600/556, 557, 587, 9, 11, 12, 13, 14, 15; 606/167, 184, 185, 189, 129, 204; 607/1, 607/2, 45, 58; 601/1, 15; 128/907
See application file for complete search history.

(56) References Cited

U.S. PATENT DOCUMENTS

| | | | |
|---|---|---|---|
| 4,161,943 A | | 7/1979 | Nogier |
| 4,262,672 A | | 4/1981 | Kief |
| 4,508,119 A | | 4/1985 | Tukamoto |
| 5,965,282 A | * | 10/1999 | Baermann ............ 428/800 |
| 6,113,620 A | | 9/2000 | Chung |
| 6,432,036 B1 | | 8/2002 | Kim |
| 6,488,668 B1 | | 12/2002 | Prindle |
| 6,783,504 B1 | | 8/2004 | Xie |
| 7,167,752 B2 | | 1/2007 | Lin-Hendel |

FOREIGN PATENT DOCUMENTS

WO    WO98/02128    1/1998

* cited by examiner

*Primary Examiner* — Jeffrey G Hoekstra
(74) *Attorney, Agent, or Firm* — Michael I. Kroll

(57) ABSTRACT

A magnetic acupuncture needle combining the treatments of magnetic therapy and acupuncture by affecting the natural magnetic bio-field of energy of the patient's body and attracting it to the target point of treatment.

2 Claims, 8 Drawing Sheets

MAGNETIC ACUPUNCTURE NEEDLE

BACKGROUND OF THE INVENTION

1. Field of the Invention

The present invention relates generally to needles and, more specifically, to a magnetized acupuncture needle that constantly and consistently attracts the movement of energy, effecting best results. With magnetism, the needle is always working after insertion. This difference in needle function can best be compared to siphoning water with a hose using the mouth to induce the siphon compared to using an electric motor. The motor is most effective, consistent and continuous in starting and maintaining the flow of water and at a consistent rate. In this case magnetism is used and the flow of electrons induced by magnetism. An unskilled practitioner will have enhanced results as the magnetized needle affects electromagnetic energy at the point, even if the practitioner has been unable to independently stimulate this reaction.

2. Description of the Prior Art

There are other medical devices designed for magnetic therapy. Typical of these is U.S. Pat. No. 4,161,943 issued to Nogier on Jul. 24, 1979.

Another patent was issued to Kief on Apr. 21, 1981 as U.S. Pat. No. 4,262,672. Yet another U.S. Pat. No. 4,508,119 was issued to Tukamoto on Apr. 2, 1985 and still yet another was issued on U.S. Pat. No. 6,113,620 to Chung as U.S. Pat. No. 6,113,620.

Another patent was issued to Kim on Aug. 13, 2002 as U.S. Pat. No. 6,432,036. Yet another U.S. Pat. No. 6,488,668 was issued to Prindle on Dec. 3, 2002. Another was issued to Xie on Aug. 31, 2004 as U.S. Pat. No. 6,783,504 and still yet another was issued on Jan. 23, 2007 to Lin-Hendel as U.S. Pat. No. 7,167,752.

Another patent was issued to Wang on Apr. 8, 1992 as China Patent No. CN1060036. Yet another International Patent Application No. WO 98/02128 was issued to Chung on Jan. 22, 1998. Another was issued to Choi on Feb. 25, 2004 as Korea Patent No. KR20040016928.

An apparatus for implanting magnetized or magnetizable needles, which apparatus comprises a tubular body, means to support a flat needle of small dimensions, made of a magnetizable metal, and means to drive the said needle into the tissues. A permanent magnet, taking the form of a substantially circular flat tablet is inserted in closed end of the body with one of its sides exposed outwardly of same. When the needle has been implanted, it may be magnetized or remagnetized as often as required by merely applying the exposed side of the tablet against the tail of the needle. In a modification the body of the apparatus is provided with a socket-like protecting cap and the tablet is inserted in the closed end of this cap, the needle supporting means being so arranged that the tip of the needle is situated close to the said closed end of the cap in order to be already magnetized by the tablet before the needle is implanted.

An acupuncture instrument for use in producing analgesia comprises a needle having a head and an electrical connection for applying a transformer arrangement including an electric coil constituting a secondary winding of the transformer arrangement and having two poles, one of the poles being insulated therefrom, the electric coil being arranged on the needle head and being capable of being surrounded by another coil constituting a primary winding of the transformer arrangement, and an annular electrode electrically connected to the other pole of the secondary winding and insulated with respect thereto and vertically movably arranged on the secondary winding.

A needle having at least one of magnetic field and electrostatic field improves effects of acupuncture in Oriental medical therapy. Further, a magnetized and/or electrostatically charged injection needle can be used for so-called "block therapy".

A magnetic needle for acupuncture is disclosed. The magnetic needle of this invention has a housing having an opening and a magnet seated in the opening of the housing. A wedge-shaped projection is held in the opening of the housing so as to project into the exterior of the bottom wall of the housing and come into contact with the magnet. The projection forms an intensive magnetic field around a meridian point having fine electric current or electromagnetic waves. The projection thus magnetically stimulates the meridian point while performing a magnetic massage effect on the meridian point. The magnetic needle accomplishes an acupuncturing effect for relieving pain and curing disease as expected in typical acupuncture.

A device for magnetic focus radiating medical treatment is disclosed. The device has a support member holding both a magnet and a needle therein in a way such that the magnet comes into contact with the needle. The magnet is used for generating lines of magnetic force, while the needle is used for radiating the lines of magnetic force from the magnet onto a desired part of the human body. A hollow casing receives the support member therein with the tip of the needle being selectively projected from the lower end of the casing. This casing has an external thread at its lower end. An outside plug detachably covers the top end of the casing. A cap is movably tightened to the external thread of the casing. This cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

A device for magnetic focus radiating medical treatment is disclosed. The device has a support member holding both a magnet and a needle therein in a way such that the magnet comes into contact with the needle. The magnet is used for generating lines of magnetic force, while the needle is used for radiating the lines of magnetic force from the magnet onto a desired part of the human body. A hollow casing receives the support member therein with the tip of the needle being selectively projected from the lower end of the casing. This casing has an external thread at its lower end. An outside plug detachably covers the top end of the casing. A cap is movably tightened to the external thread of the casing. This cap also has a needle hole at a central portion of its wall so as to allow the needle to pass through the needle hole. In the above device, the exposed length of the needle outside the cap is adjustable as desired by appropriately tightening or loosening the internally threaded cap relative to the externally threaded casing.

A method for effective weight loss without negative or harmful side effects as well as for the treatment of ailments in human patients. Treatment is achieved using a combination of acupuncture and magnets. The method includes the steps of placing several acupuncture needles into specified locations on the human body, removing the acupuncture needles, and placing several magnets onto the same locations that the needles previously occupied. Another important object of the present invention is to provide and effective method of coping with and managing diabetes.

An electronic acupressure aide and stimulating device implemented using a hand-held or palm-held electronic computing device or another computing device which may be a designated unit. The electronic acupressure aide and stimulating device allows a practitioner to apply a pulse sequence to a set of predetermined acu-points such as those related to acupressure, acupuncture, trigger points or Jin-Shin Jyutsu, to name a few. A displayed chart related to the acu-points identifies the health condition and the pulse sequence.

The present invention relates to a kind of miniature strong magnetism therapeutic device which is composed of a dia 24 mm multiply 27 mm Nd—Fe—B permanent magnet, a dia 24 mm bottom, dia 3 mm top and 10 mm height conoid which is punched a 2 mm straight hole on centre, and aluminum alloy casing and housing. The magnetic field intensity at top surface of said invention is 6000 Gauss. When it is used for massage or needle press on affected part or acupuncture point, the magnetic beam with penetrating feeling is radiated on human body to improve the blood circulation of local muscle or joint and to variate the excitation and inhibition of central nervous system, thus producing the analgesic action. If it is used for curing muscular spasm, lumbocrural pain, arthritis and neuralgia, it has quick analgesic and antispasm curative effects and no by-effects.

A magnetic needle for acupuncture is disclosed. The magnetic needle of this invention has a housing having an opening and a magnet seated in the opening of the housing. A wedge-shaped projection is held in the opening of the housing so as to project into the exterior of the bottom wall of the housing and come into contact with the magnet. The projection forms an intensive magnetic field around a meridian point having fine electric current or electromagnetic waves. The projection thus magnetically stimulates the meridian point while performing a magnetic massage effect on the meridian point. The magnetic needle accomplishes an acupuncturing effect for relieving pain and curing disease as expected in typical acupuncture.

PURPOSE: Provided are an acupuncture needle using bamboo, charcoal and a magnet having beneficial effects on the human body, and a manufacturing method thereof, to suppress pain by pressing acupuncture spots and to enhance a user's health and vitality by stimulating blood circulation and generating far-infrared radiation. CONSTITUTION: The acupuncture needle (6) comprises: a bamboo cylinder (2); an energy radiating plate (1) and a circular magnet (3) provided at a bamboo node (4); and a charcoal rod (5) filling the bamboo cylinder (2). The acupuncture needle is prepared by putting a circular magnet and a charcoal rod into the bamboo cylinder and sealing with the energy radiating plate.

While these processes may be suitable for the purposes for which they were designed, they would not be as suitable for the purposes of the present invention, as hereinafter described.

SUMMARY OF THE PRESENT INVENTION

Acupuncture is a medical treatment using needles inserted at specific locations to treat illness, pain and to enhance the flow of Qi in establishing health and well-being within a patient. Magnetism has been applied in this treatment through ancillary devices used to create a magnetic field within the needle. The present invention has combined the magnetic field and acupuncture needle therapy into a single device by permanently magnetizing the needles with either a north-south polarity or a south-north polarity thereby eliminating the need for ancillary devices to induce a magnetic field within the needle simplifying treatment.

The magnetic needles of the present invention may replace electro-stimulation of standard acupuncture needles as well as enhance the effects achieved by advances acupuncture practitioners for those patients having difficulty inducing the movement of the body's energy and the elderly whose body energy has weakened and does not circulate well.

Some of the advantages of using magnetized needles are as follows:

a) The effects that surface magnets provide is also achieved but more powerful due to the magnetized needle actually being inserted into the point and directly into the body's bioelectric/magnetic field rather than near the field on the surface;

b) A much smaller magnetic force is required with insertion compared to the larger (often 3000 gauss or more) when used directly on the skin;

c) Needles may be magnetized with poles N—S or S—N and the varied effect of the needle would be available at the discrimination of the practitioner;

d) By inserting a N—S needle into a point and a S—N needle very nearby in the same point or pathway one may create additional magnetic stimulation to the bioenergetic circulation, literally forcing, rather than inducing, the bioelectric flow; and e) As acupuncture pathways are distinct and proscribed in medical literature one may select points up and down the meridians, or energetic pathways, and combine several magnetized needles but not only N—S, one may perhaps alternate N—S, S—N, and so on.

Other advantages of the magnetized needles can be applied to other afflictions including addictions and weight loss. Smaller needles are sometimes inserted into auricular (ear) points to stimulate the micro-acupuncture system found in each persons (or animals) ears. Some of these points are used for weight loss, some for addictions and most other conditions may be affected.

A primary object of the present invention is to provide a magnetized acupuncture needle.

Another object of the present invention is to provide an acupuncture needle having either a north-south polarity or a south-north polarity.

Additional objects of the present invention will appear as the description proceeds.

The present invention overcomes the shortcomings of the prior art by providing a magnetized acupuncture needle that constantly and consistently attracts the movement of energy, effecting best results. With magnetism, the needle is always working after insertion. This difference in needle function can best be compared to siphoning water with a hose using the mouth to induce the siphon compared to using an electric motor. The motor is most effective, consistent and continuous in starting and maintaining the flow of water and at a consistent rate. In this case magnetism is used and the flow of electrons induced by magnetism. An unskilled practitioner will have enhanced results as the magnetized needle affects electromagnetic energy at the point, even if the practitioner has been unable to independently stimulate this reaction.

The foregoing and other objects and advantages will appear from the description to follow. In the description reference is made to the accompanying drawings, which forms a part hereof, and in which is shown by way of illustration specific embodiments in which the invention may be practiced. These embodiments will be described in sufficient detail to enable those skilled in the art to practice the invention, and it is to be understood that other embodiments may be utilized and that structural changes may be made without departing from the scope of the invention. In the accompanying drawings, like reference characters designate the same or similar parts throughout the several views.

The following detailed description is, therefore, not to be taken in a limiting sense, and the scope of the present invention is best defined by the appended claims.

BRIEF DESCRIPTION OF THE DRAWING FIGURES

In order that the invention may be more fully understood, it will now be described, by way of example, with reference to the accompanying drawing in which.

DESCRIPTION OF THE REFERENCED NUMERALS

Figure 1:
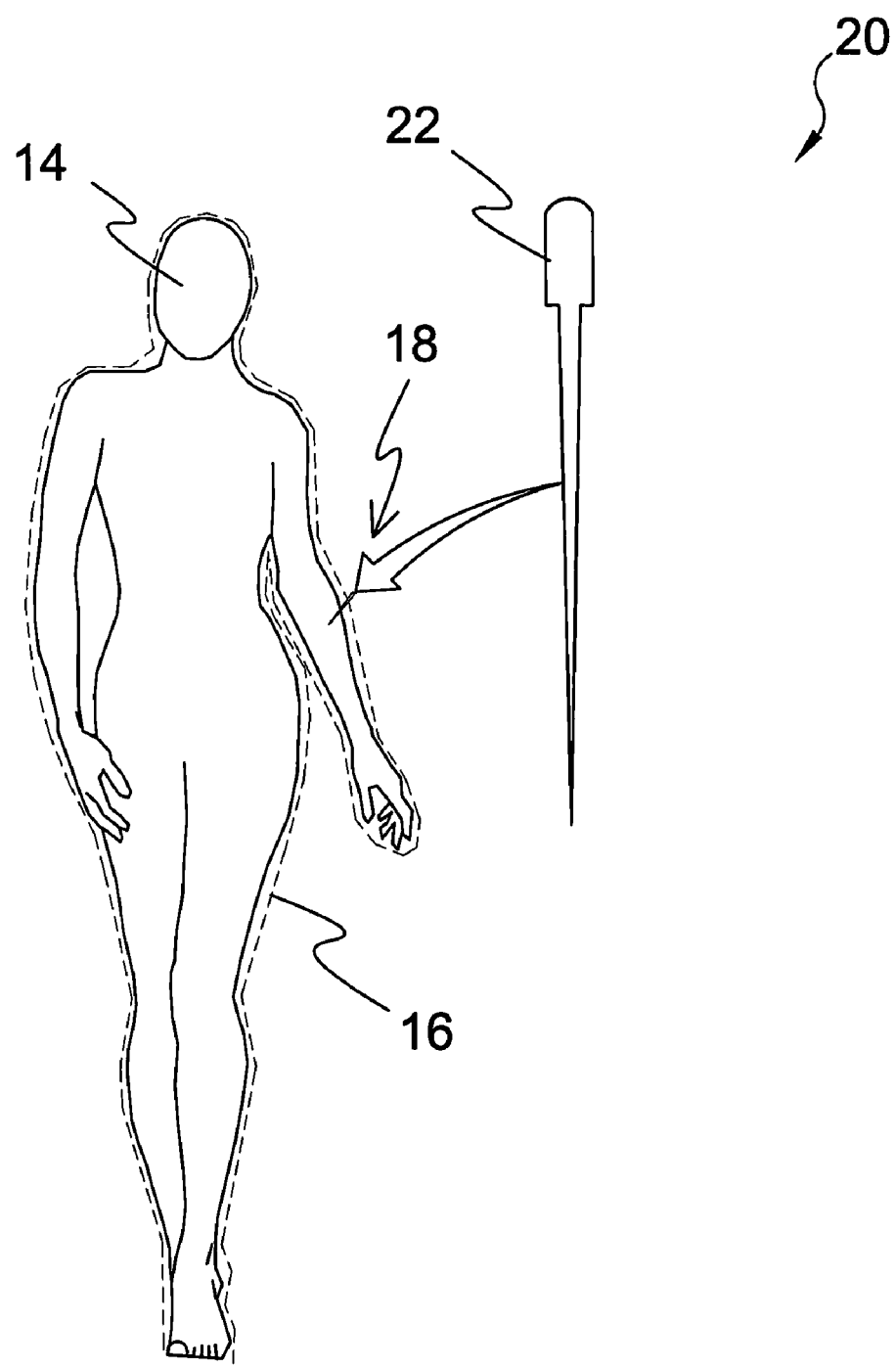
FIG. 1 is an illustrative view of prior art.

Turning now descriptively to the drawings, in which similar reference characters denote similar elements throughout the several views, the figures illustrate the Magnetic Acupuncture Needle of the present invention. With regard to the reference numerals used, the following numbering is used throughout the various drawing figures.

10 Magnetic Acupuncture Needle of the present invention
12 electromagnetic charge of 10
14 patient's body
16 magnetic bio-field of energy of 14
18 acupuncture meridian target point
20 prior art
22 non-magnetic acupuncture needle of 20
24 head of 10
25 shaft of 10
26 point of 10
28 northern polarity of 12
30 southern polarity of 12
32 north to south needle
34 south to north needle
36 needle receptor
38 ear press tack needle

DETAILED DESCRIPTION OF THE PREFERRED EMBODIMENT

The following discussion describes in detail one embodiment of the invention (and several variations of that embodiment). This discussion should not be construed, however, as limiting the invention to those particular embodiments, practitioners skilled in the art will recognize numerous other embodiments as well. For definition of the complete scope of the invention, the reader is directed to appended claims.

FIG. 1 is an illustrative view of prior art 20. Acupuncture is an eastern medicine that relies upon fine sterile non-magnetic metal needles 22 inserted into specific points 18 on the body 14. The theory is that there is a constant circulation of a magnetic bio-field of energy 16 in the body and that when the energy flow is obstructed by natural or traumatic means, a corresponding disease will eventually manifest. Keeping this flow of energy undisturbed is the goal of acupuncture. Some practitioners using non-magnetic needles 22 are more skilled at needle manipulation and the sensation at the needle. A non-magnetized acupuncture needle 22 is dependent upon the practitioners' skill to induce a result. The present invention over comes this by providing a magnetized acupuncture needle.

Figure 2:
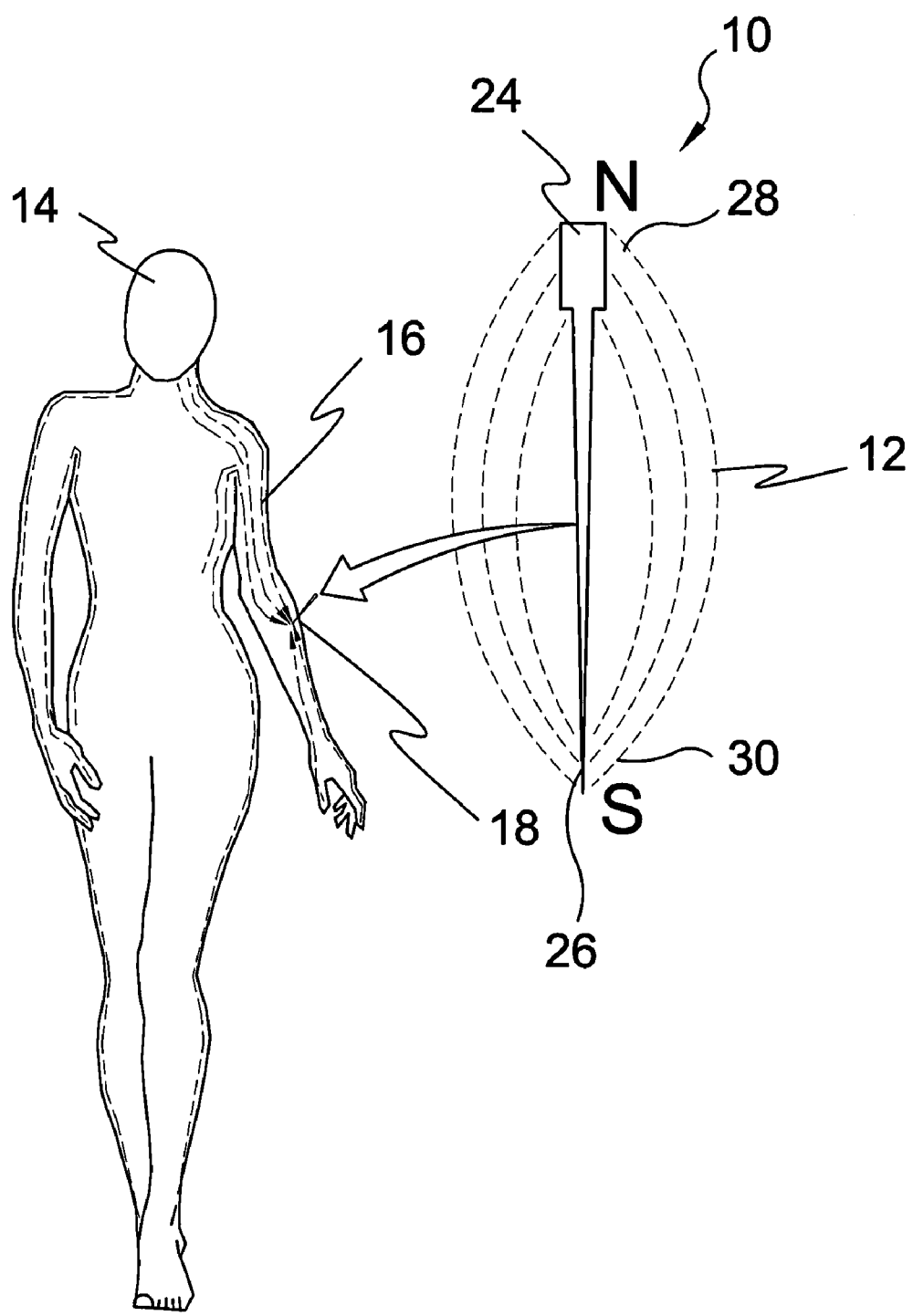
FIG. 2 is an illustrative view of the present invention.

FIG. 2 is an illustrative view of the present invention 10. The present invention is a magnetized acupuncture needle 10 having an electromagnetic charge 12 that constantly and consistently attracts the movement of the magnetic bio-field of energy 16 produced by the patient's body 14, effecting best results. With magnetism, the needle 10 is always working after insertion. This difference in needle function can best be compared to siphoning water with a hose using the mouth to induce the siphon compared to using an electric motor. The motor is most effective, consistent and continuous in starting and maintaining the flow of water and at a consistent rate. In this case magnetism is used and the flow of electrons induced by magnetism. An unskilled practitioner will have enhanced results as the magnetized needle 10 effects electromagnetic energy at the insertion point 18, even if the practitioner has been unable to independently stimulate this reaction. The needle 10 has a head 24 with a northern polarity 28 and a point 26 with a southern polarity 30.

Figure 3:
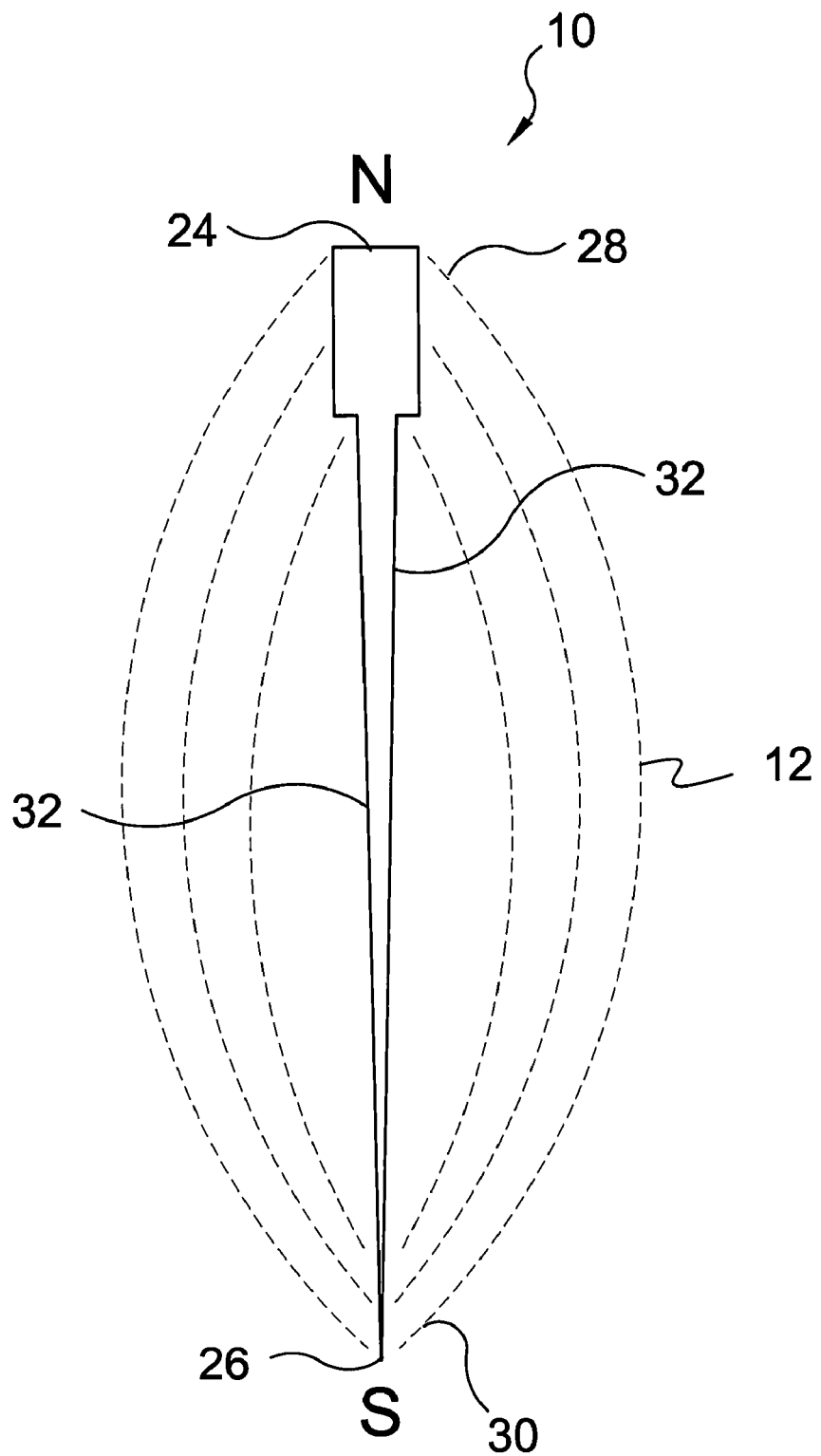
FIG. 3 is an illustrative view of the magnetized acupuncture needle having a north to south polarity.

FIG. 3 is an illustrative view of the magnetized acupuncture needle 10 having a magnetic field charge 12 with a north 28 to south polarity 30 from the head 24 to the point 26. A shaft 25 is disposed between the head 24 and the point 26. Shown is the magnetized acupuncture needle 10 of the present invention that constantly and consistently attracts the movement of energy. With magnetism, the needle 10 is always working after insertion because the flow of electrons induced by magnetism are constant and induces the bio-field of energy to move or flow constantly through the body. The north to south polarity magnetic needle 32 could be used alone or in conjunction with a south to north polarity magnetic needle.

Figure 4:
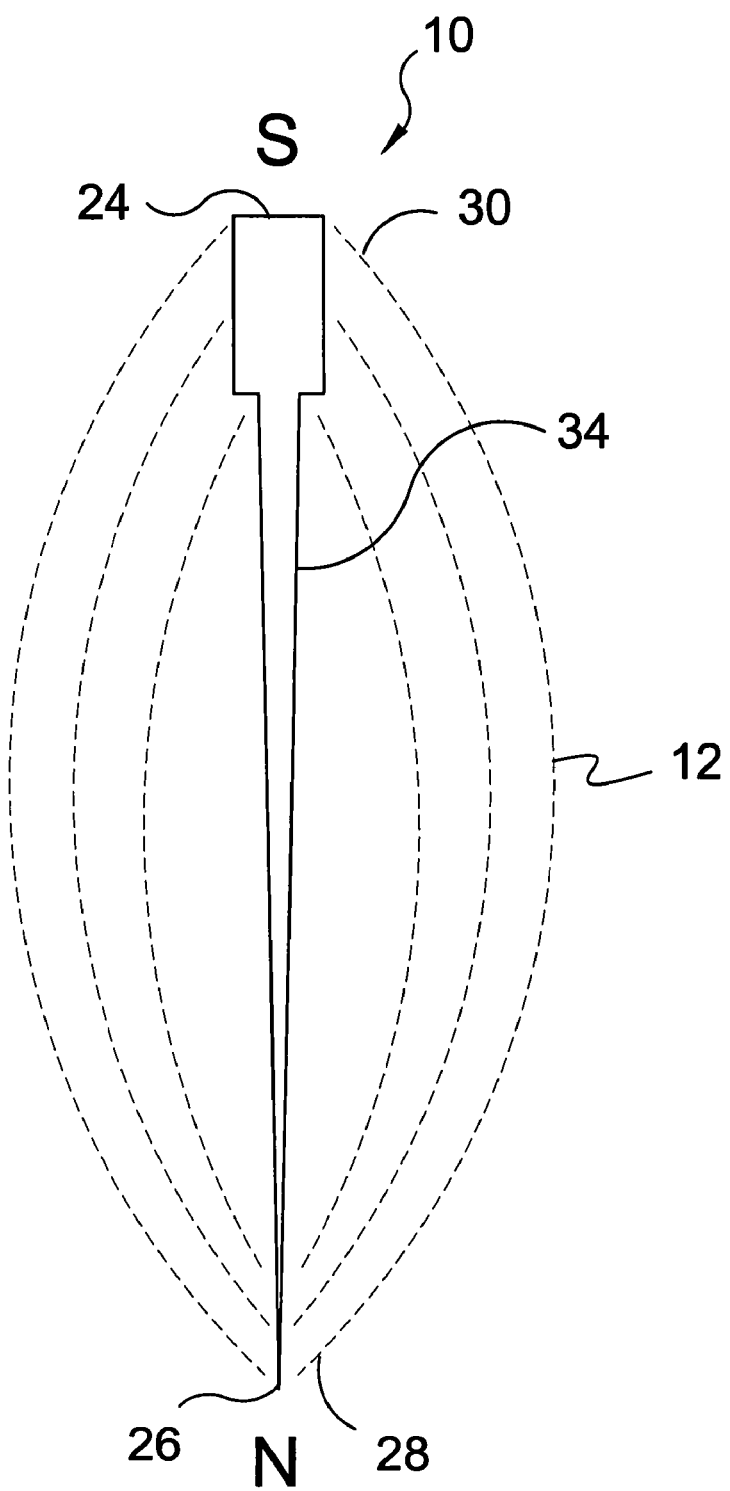
FIG. 4 is an illustrative view of the magnetized acupuncture needle having a south to north polarity.

FIG. 4 is an illustrative view of the magnetized acupuncture needle 10 having a magnetic field charge 12 with a south 30 to north polarity 28 from the head 24 to the point 26. The south to north polarity needle 34 could be used alone or in conjunction with a north to south polarity needle.

Figure 5:
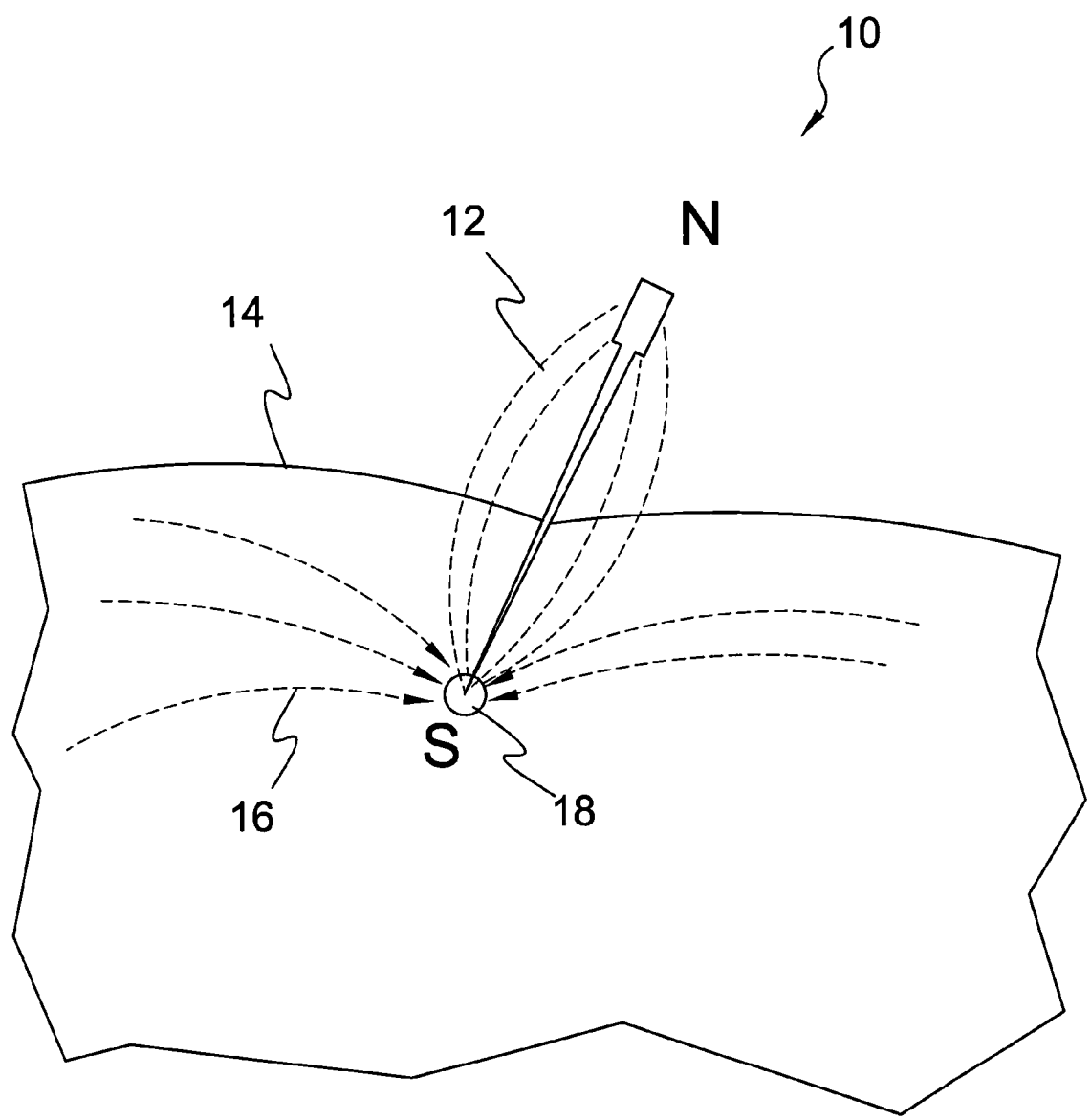
FIG. 5 is an illustrative view of the application of the present invention.

FIG. 5 is an illustrative view of the application of the present invention 10. Shown is biological electromagnetic field 16 enhanced by the insertion of a permanent magnet. The magnetic acupuncture needle 10 is inserted into a predetermined acupuncture meridian-target insertion point 18 to induce the flow of a body's energy by using the electrical charge 12 of the magnetized needle 10 as a connective member to reestablish the bio-field of energy 16 to move or flow constantly through the patients body 14. While depicted as a north to south magnetized needle 10, the present invention provides for either north to south or south to north magnetized needles 10 that may be used in combination with each other.

Figure 6:
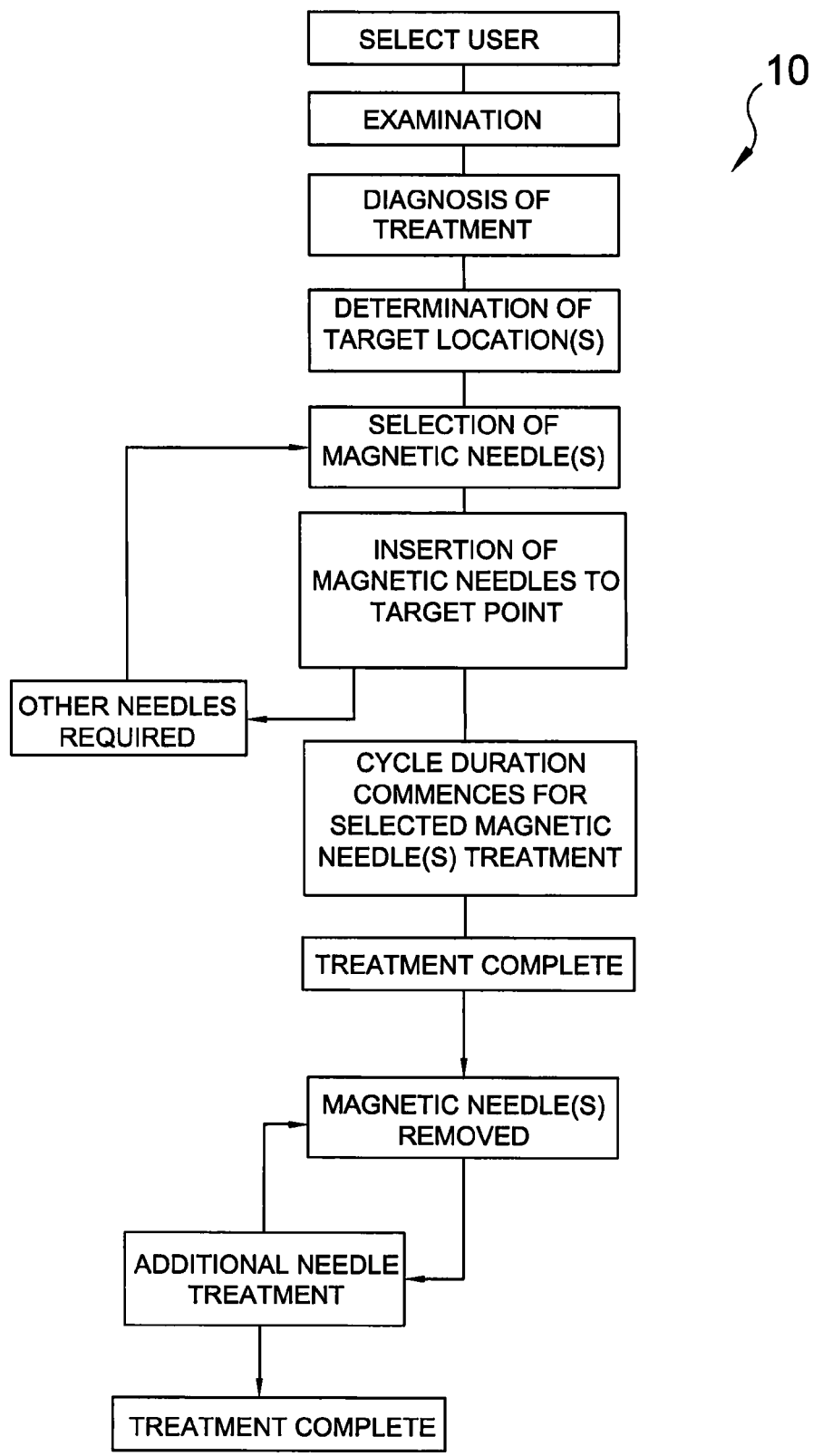
FIG. 6 is a flow chart of the acupuncture therapy using magnetized needles.

FIG. 6 is a flow chart of the acupuncture therapy using magnetized needles 10 including the steps of selecting and examining the patient, making a diagnosis and determining the target insertion locations, and selecting and inserting the magnetized acupuncture needles 10.

Figure 7:
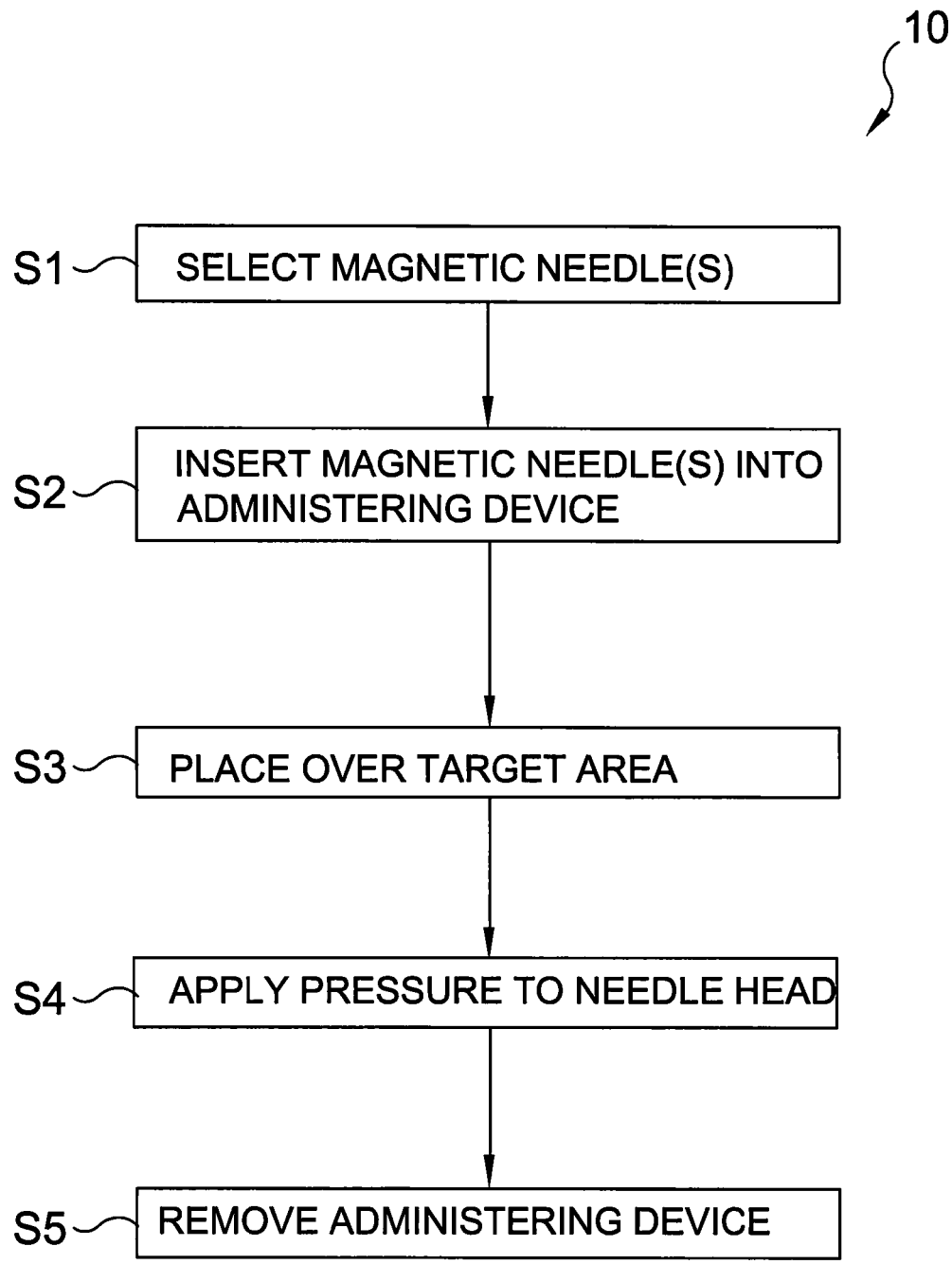
FIG. 7 is a flow chart of the present invention.

FIG. 7 is a flow chart of the present invention 10. Shown is a flow chart of the method for enhancing the flow of electrons induced by magnetism including the steps of selecting the needles 10, inserting the needles 10 into an administering device, placing the tip of the needle 10 over the target area, applying pressure to the head of the needle 10 to insert it therein and removing the administering device.

Figure 8:
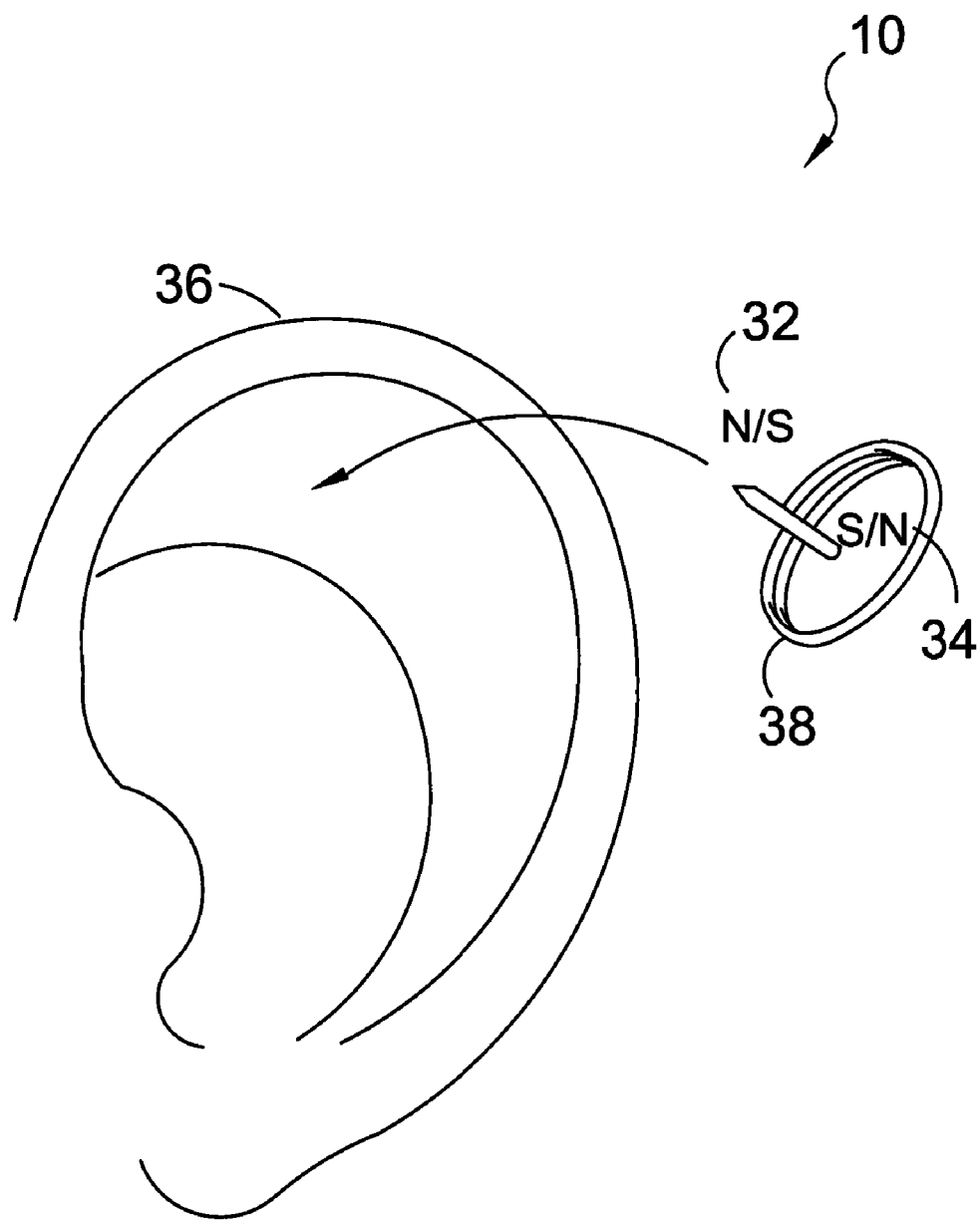
FIG. 8 is another illustration of the present invention in use as a tack needle.

FIG. 8 is an illustrative view of the magnetized acupuncture needle 10 manufactured as an ear press tack needle 38 for an ear 36 having a magnetic field comprising either a north to south polarity 32 or a south to north polarity 34 needle.

It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by letters patent is set forth in the appended claims:

1. A method of increasing the biological electro-magnetic field at a specific location of a patient's body through the use of a set acupuncture needles having a permanent magnetic charge with a north to south polarity from head to point and a set having a north to south polarity from point to head including the steps of:
    providing a first set of acupuncture needles have a permanent magnetic charge with a north to south polarity from a head to a sharp point, the sharp point for insertion into epidermal tissue of the patient;
    providing a second set of acupuncture needles have a permanent magnetic charge with a north to south polarity from a sharp point to a head, the sharp point for insertion into epidermal tissue of the patient;
    examining the patient;
    diagnosing results of the examination;
    determining the acupuncture meridian target insertion points;
    selecting a plurality of needles from said first set of acupuncture needles;
    inserting said plurality of needles into said target insertion points where the sharp points of each needle pierce the epidermal tissue of the patient;
    increasing a flow of a natural bio-field of energy to each meridian point through magnetic attraction to said plurality of needles from said first set of acupuncture needles;
    selecting a needle from said second set of acupuncture needles and inserting said needle from said second set at a location proximal to but spaced from one of the needles from said plurality of needles from said first set where the sharp point of the needle from the second set pierces the epidermal tissue of the patient;
    leaving all the needles in their respective insertion points for a pre-selected period of time; and
    removing all the inserted needles.

2. The method of claim 1, wherein the head of each of the needles of the first and second set of needles is joined to its respective sharp point by an elongate shaft that is narrower than its respective head, and each head has a rectangular shape.

* * * * *